United States Patent
Freadman et al.

(10) Patent No.: US 6,589,761 B1
(45) Date of Patent: Jul. 8, 2003

(54) METHOD AND APPARATUS FOR DETECTING BACTERIA

(76) Inventors: Marv Freadman, 201 Marginal St., Chelsea, MA (US) 02150; Howard C. Beach, 70 Belcher Cir., Milton, MA (US) 02186

( * ) Notice: Subject to any disclaimer, the term of this patent is extended or adjusted under 35 U.S.C. 154(b) by 0 days.

(21) Appl. No.: 09/661,349

(22) Filed: Sep. 14, 2000

Related U.S. Application Data

(60) Provisional application No. 60/140,052, filed on Jun. 19, 1999.

(51) Int. Cl.⁷ .............................. C12Q 1/02; C12Q 1/18; G01N 33/53
(52) U.S. Cl. ..................... 435/29; 435/32; 435/287.5; 435/283.1; 435/807; 435/287.1; 435/968
(58) Field of Search ............................. 435/34, 29, 32, 435/287.5, 283.1, 807, 287.1, 968

(56) References Cited

U.S. PATENT DOCUMENTS 5,795,773 A  *  8/1998  Read et al. .............. 435/286.6

* cited by examiner

*Primary Examiner*—Louise N. Leary
(74) *Attorney, Agent, or Firm*—John M. Brandt

(57) ABSTRACT

A device and method for detecting bacteria in food substances and the like utilizing a three layer composite consisting of a transparent base, an indicator exhibiting color change when exposed to changes in pH, and a gas permeable cover placeable in proximity to the substance. The method utilizes the generation of $CO_2$ gas as a byproduct of bacterial growth which produces carbonic acid lowering the pH of the substance in the region of the composite resulting in an observable color change as in indication of the presence of bacteria.

28 Claims, 1 Drawing Sheet

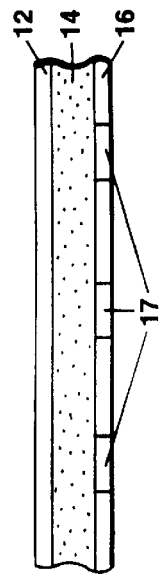
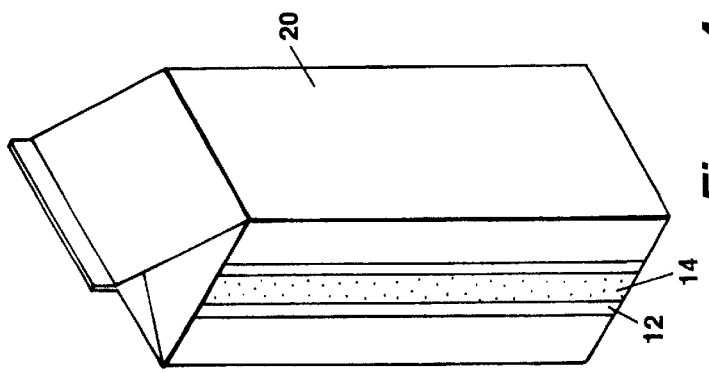
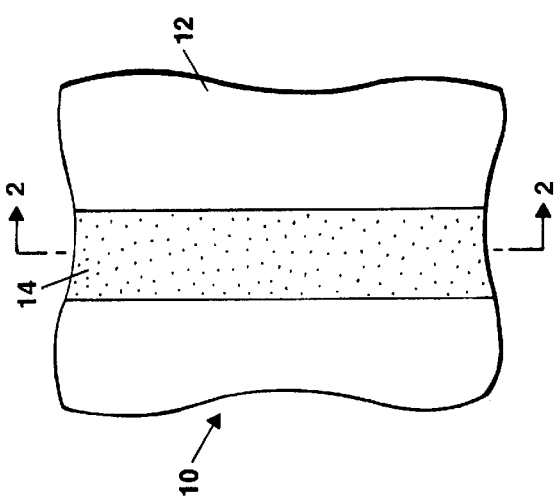
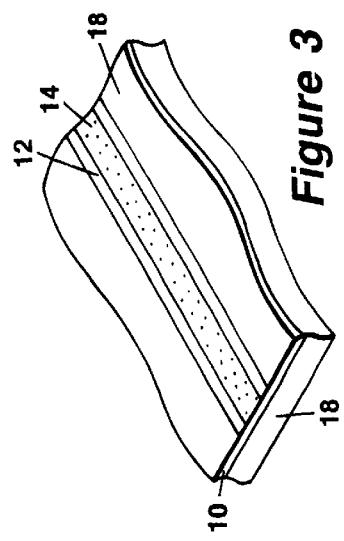

METHOD AND APPARATUS FOR DETECTING BACTERIA

CROSS-REFERENCE TO RELATED APPLICATIONS

This application is a formal application based on the disclosure of provisional application Ser. No. 60/140,052 filed Jun. 19, 1999 by the same inventors.

BACKGROUND OF THE INVENTION

Field of the invention: The invention resides in the field of bacteria detection and more particularly relates to a method and apparatus for real time indication of bacterial presence.

Description of the prior art: From the 1950's through the early 1970's, most of the recognized causes of foodborne diseases and outbreaks were related to handling of foodstuff, for example, contaminated hands, insufficient cooking and improper storage by consumers or improper food preparation. In the 1990's, it is more frequent that single source outbreaks come from unsafe sources of food. The Center For Disease Control has estimated that each American has had at least one episode of foodborne disease per year, whether it is recognized or not. Another estimate projected that, annually, between 8 and 80 million people experience foodborne illnesses and some 9,000 die.

Present methods of bacterial detection known to the inventors include incubation, DNA polymerase chain reaction, toxin detection, and protein product degradation. In contrast to the above, we have devised a real time method to detect the presence of the major bacteria known to be the cause of foodborne disease, common source outbreaks and bacterial foodstuff spoilage.

The method of detecting bacteria we have devised is also directly applicable to ensuring the sterility of medical packaging, the safety of bottled water, biological weapons detection, drug testing and the safety of surgical suites.

SUMMARY OF THE INVENTION

The detection method of the invention is based on means to detect the production of $CO_2$, a gas normally produced during the life processes of bacteria responsible for foodborne illnesses. The detection means comprises a package which is placed in close proximity to foodstuff of concern at the point of sale or consumer level. The method of detection is the use of a pH indicator which will respond to the presence of $CO_2$ gas by a change in color. An indicator is placed under currently utilized packaging for products such as meat, fish, chicken, turkey and pork, in the middle layer of a three layer package for milk, and as a button in a bottle cap for many juices. The indicator in the packaging will not affect the integrity of the foodstuff. Our detection method is applicable to the major known bacteria which taint food and cause foodborne illnesses. A large number of chemical indicators which will serve the purpose of the invention are available and will be disclosed in detail in the description of the preferred embodiment which follows.

DESCRIPTION OF THE DRAWINGS

FIG. 1 is a plan view of the preferred embodiment of the invention;

FIG. 2 is a cross-sectional view of FIG. 1 along line A—A;

FIG. 3 is a perspective view of the preferred embodiment incorporated into a food package; and FIG. 4 is a perspective view of the preferred embodiment incorporated into an alternative food package.

DESCRIPTION OF THE PREFERRED EMBODIMENT

The detection of foodborne bacteria is pivotal for prevention of foodborne illnesses. This invention detects bacteria by a device incorporateable directly into currently used packaging. The basis of the method is the detection of $CO_2$, a gas produced during the life processes of bacteria which cause foodborne illnesses. The method of detection is a pH indicator such as phenolpthalein or indole red which will change color in the presence of $CO_2$ gas by the following reaction:

$$CO_2 + H_2OH_2CO_3H + HCO_3$$

In the increasing presence of $CO_2$, the hydrogen ion concentration increases. The pH will thereupon decrease which will be detected by the pH sensitive material or indicator employed in the method. As pH is a measure of hydrogen ion concentration, the indicator incorporated into a suitable package changes color which can easily be seen by the consumer. The change in color is therefore directly related to $CO_2$ production by disease causing bacteria.

The method of detection of the invention is sensitive to small changes in pH, which in turn insensitive to low concentrations of bacteria. This is important for the detection of even a very low level of deleterious bacteria which can cause foodborne illness and for other applications as well.

This instantaneous detection method is ideally suited for all of the major bacteria that are connected to foodborne diseases. In contrast to prior art, the method of the invention does not rely on culturing techniques that must be tailored to the specific pathogen which techniques have limited use in the prevention of bacterial exposure.

The bacterial species our method detects include *Salmonella enteriitidis, Campylobacter jejuni, Escherichia coli,* including 0157:H7 and other less common shiga toxin producers, *Staphylococcus aureus, Shigella dysenteriae,* and *Listeria monocytogenes.* The method may also detect the presence of other foodborne disease causing organisms such as *Vibrio cholerae, Yersinia enterocolitica* and Acromonas sp.

The present day consumer food network is a complex system including production, processing, distribution, and consumption. This method is effective in that from whatever level it is wrapped, continuous monitoring of the packaged foodstuff can take place. Monitoring will continue in the consumer's household in the store bought package or in another package such as a sealable bag using indicator packets for leftovers to detect pathogenic organisms and spoilage due to bacteria. Monitoring will also continue when distribution is to restaurants, airport catering services, or other public distribution site.

Referring next to FIGS. 1 and 2, the indicator or sensor is incorporated in the packaging 10 which comprises, for example, a triple layer plastic wrap. The outer plastic layer 12 is not $CO_2$ permeable which protects the indicator from ambient levels of $CO_2$ and protects the foodstuff as with current wrapping. An example of a plastic which has been found to work well is polyethylene terephthalate. The middle layer 14 contains the indicator in stripes as a solid or semi-solid gel that does not bleed, thus maintaining the integrity of the foodstuff The inner plastic layer 16 is in direct contact with the foodstuff and is permeable to $CO_2$, through, for example, mechanical perforations 17 or by the use of a plastic which is in and of itself permeable to $CO_2$ such as polyethylene.

The sensor or indicator may be located in a strip across, crisscrossing or evenly distributed throughout the plastic wrap, as would be appropriate for packaged chicken, turkey, ground beef, fish and other solid or semi-solid foodstuff 18 and as is illustrated in FIG. 3.

The three-layer wrap or package of the invention with the indicator in the middle layer may be used for any food product. Alternatively, for packaged meats including sliced variations and hot dogs, pork, chicken and turkey, a triple layer packet of defined size is included with the sensor or detector under conventional packaging. In addition, a similar unit could be incorporated into a button or wafer and placed in a cap for juices or bottled water.

As shown in FIG. 4, for liquid containers, for example, for milk or non-carbonated juice, the three layer composite of the invention may be located in a strip down the side of and forming an integral part of container 20.

The method utilizing the above described device for detecting bacterial growth in a substance wherein a byproduct of the growth is carbon dioxide which, in the presence of ambient water, results in the production of carbonic acid yielding an increase in hydrogen ion concentration and a decrease in pH is as follows:

Provide the above described C02 impermeable transparent support base and dispose thereon a quantity of an indicator having the property of exhibiting a color change upon exposure to a decrease in pH. Thereafter provide the above described CO2 permeable cover and dispose it over the indicator to provide a composite and thereafter place the above described composite in proximity to the subject substance to provide an indication of bacterial growth through the observable color change of the indicator. In the above described method, the indicator may be combined with a gel and may be characterized as of one or more of a variety of indicators to be further listed below including an acid base, mixed, screened, universal, plant derived, fluorescent, luminescent, irreversible, or miscellaneous indicator. Additionally, the composite may consist of a sheet food wrap, a portion of a container for liquids, and or a wafer of appropriate size.

A large variety of indicators have been determined to work to detect $CO_2$ produced by the bacterial species listed earlier in the specification. The detection occurs as $CO_2$ produced by the bacteria migrates into the indicator mixed in agar or gelatin, semi-solid or solid, and causes a change in pH of the indicator-gel environment. The result is a change in the color of the indicator which is indicative of the presence of bacteria which can cause foodborne illness. The sensitivity of the indicator-gel (agar or gelatin based detector) can be adjusted to detect various concentrations of bacterial species. The concentrations of the indicators can be varied to take into account potential risks of contamination. Suitable indicators may also include natural indicators in the form of compounds derived from plants such as beets or cabbage. The agar or gelatin base with which the indicator is combined will not harm the integrity of the foodstuff. Further, the list of workable indicators includes compounds which differ in their pH ranges and color changes. It is also contemplated that two or more indicators may be mixed to provide greater flexibility in designing suitable packages for various applications.

It has been determined that all indicators listed below work to detect the presence of bacterial species responsible for foodborne illness. The indicator-gel combination undergoes a change in pH and hence, color change, as a result of the production of $CO_2$ by bacteria.

For all applications of concern, if bacteria are not present, the indicator will not change color. It is expected that through experimentation, modifications and refinements can be carried out to determine the best indicator-gel detection system based on bacterial species concentration, indicator concentration, temperature, and expected illumination of the completed package as determined by the specific application of the method.

The indicators listed below comprise various groups of indicators. The groups are regular acid-base indicators, mixed indicators, screened indicators, universal indicators, pH sticks, litmus paper (embedded in gel or litmus in a gel), natural food indicators, fluorescent indicators, luminescent indicators, irreversible indicators and a miscellaneous group. Many of these indicators can exist either in a water soluble form or an alcohol based form. Indicators that have been found to work include but are not limited to:

ACID-BASE INDICATORS:

Acid Fuchsin (red-yellow)
Alkali Blue 6B Solution (alcoholic blue-red titrations)
Alizarin (yellow-red)
Alizarin Red S (yellow-red)
Alizarin Yellow R (yellow-red)
Alizarin Complexone, dihydrate (yellow-red)
Andrade indicator with agar (yellow-red)
Anilinesulfonphthalein (colorless-yellow)
Aniline yellow (colorless-yellow)
Arsenazo (black/purple-light blue)
Azolitmin (red-blue)
Azo violet (red/brown-yellow)
Benzopupurine (violet-red)
Bindschedlers green (green-yellow)
2,2'-Bipyridyl (orange-light yellow)
4,4'-Bis(2-amino-1-napthylazo) 2,2-stilbenedisulfonic acid (purple-red)
4,4'-Bis(4-amino-1-napthylazo) 2,2-stilbenedisulfonic acid (brown-red)
Brilliant Green (yellow-green)
Brilliant Orange (yellow-red)
Brilliant Yellow (yellow-red)
Bromocresol Green (yellow-blue)
Bromocresol Purple (yellow-purple)
Bromochlorophenol Blue (yellow-blue/violet)
Bromophenol Blue (yellow-blue)
Bromophenol Red (yellow-red)
Bromopyrogallol Red (yellow-red)
Bromothymol Blue (yellow-blue)
Bromoxylenol Blue (yellow-blue)
Calcein/Fluorexon (orange-light yellow)
Calconcarboxylic Acid (orange-yellow)
Calmagite (dark brown-light yellow)
Carboxyarsenazo III (dark brown-light blue/yellow)
Chlorophenol Red (yellow-red)
Clayton Red (yellow-red)
Clayton Yellow (yellow-amber)
Cochineral (orange-yellow)
Congo Red (blue-red)
o-Cresolphthalein (red-yellow)

Cresol Purple (red-yellow)
Cresol Red, 1st and 2nd range (red-yellow)
Crystal Red (yellow-blue)
Cresolphthalein (yellow-red)
Crystal Violet (yellow-blue)
Curcumin (Tumaric) (yellow-red)
Cyanide Acid Blue (blue-red)
Debrisoquine sulfate 3,4-Dihydro-2-[1H]-isoquinoli (yellow-red)
p-(2,4 Dihydroxyphenylazo) benzenesulfonic acid, sodium salt ((yellow-orange)
p-Dimethylaminoazobenzene (red-yellow)
4-(n,N-Dimethylamino)azobenzene (red-yellow)
N 2,n2-dimethylquanosine (red-yellow)
4-(4-Dimethylamino-1-naphylazo)-3-methoxybenzenesulfonic acid (violet-yellow)
3-(4-Dimethylamino-1-naphylazo)-4-methoxybenzene (violet-yellow)
2-(p-Dimethylaminophenylazo)pyridine (yellow-blue)
Dimethylsulfonazo III (yellow-blue)
Diphenylalanine-4-sulfonic acid barium salt (yellow-blue)
Diphenyl-4-Sulfonic acid sodium salt (yellow-blue)
N,N-Dimethyl-p-(m-tolylazo)anlline (red-yellow)
2,4-Dinitrophenol (colorless-yellow)
2,5-Dinitrophenol (colorless-yellow)
2,6-Dinitrophenol (colorless-yellow)
Diphenol Purple (yellow-purple)
2-(2,4 Dinitrophenylazo)-1-naphthol-3,6-disulfonic acid, sodium salt (yellow-red)
6,8-Dinitro-2,4-(1H)quinazolinedione (colorless-yellow)
Diphenylalanine (yellow-blue)
Diphenylalanine-4-sulfonic acid sodium salt (yellow-blue)
Eosin (pink-red/purple)
Epsilon Blue (orange-violet)
Erichrome Blue Black R (blue/black-violet)
Erythrosin, disodium salt (orange-red)
4-(p-Ethoxyphenalzo)-m-phenylene-diamine monohydrochloride (orange-yellow)
Ethyl bis(2,4-dimethylphenyl) ethanoate (colorless-blue)
Ethyl Orange (red-yellow)
Ethyl Red (colorless-red)
Ethyl Violet (yellow-blue)
Fast Sulphon Black F (black-light blue/yellow)
Ferroin Solution (red-green)
Fluorexon (yellow-blue)
Hematoxylln (brown-yellow)
8-hydroxypyrene-1,3,6-trisulfonic acid (colorless-blue)
Indigo Carmine (blue-yellow)
5,5'-Indigodisulfonic acid, disodium salt (blue-yellow)
Indigo Trisulfonate Potassium Salt (blue-yellow)
Indole Pentasodium (blue-yellow)
Indolphenol Sodium Salt (blue-yellow)
Leucocrystal violet (blue-yellow)
Litmus (Azolitmin) (red-yellow)
Malachite Green (yellow-blue/green)
Metacresol Purple (red-purple)
Metanil Yellow (red-yellow)
Methylene Blue (deep green-blue)
Methyl Green (yellow-blue)
4-Methylumbelliferone methyleneminodiacetic acid (red-orange)
Methyl Orange (red orange)
Methyl Purple (red-orange)
Methyl Red (red -yellow)
Methylthymol Blue (green/brown-yellow)
Methyl Violet (yellow-blue)
Methyl Viologen (yellow-blue)
Methyl Yellow (colorless-yellow)
Murexide Powder (deep red-yellow)
1-Naphthobenzein (yellow-green)
o-Naphtholbenzein (yellow-green)
p-Naphtholbenzein (yellow-blue)
a-Naphthoflavone (yellow-blue)
Naphtholphthalein (yellow-blue)
1-Naphthyl Red (yellow-blue)
Neutral Red (red-yellow)
Nitramine (colorless-orange/brown)
Nitroaniline (yellow-green)
Nitrazine Yellow Powder (yellow-green)
4-Nitrophenol (colorless-yellow)
3-Nitrophenol (colorless-yellow)
p-Nitrophenol (colorless-yellow)
Nitrosulfonazo III (colorless-yellow)
Orange G (red-yellow)
Orange 1 (Tropaeolin 000 No. 1) (rose-yellow)
m-Orange IV (Tropaeolin 00) (red-yellow)
Oregon Green/derivatives like Oregon Green carboxylic acid (deep green-yellow)
Paramethyl Red (red-yellow)
Patent Blue (deep blue-yellow)
1,10-Phenolanthronine (colorless-yellow)
5-Nitro-1,10-phenanthroline hydrate (colorless-pink)
Phenolpthalein (colorless-pink)
Phenolphthalin 2-[Bis4-hydroxyphenylmethyl]benzoic (colorless-pink)
Phenol Red (yellow-red)
Phenol Red Sodium Salt (yellow-red)
Phenol Violet (yellow-blue)
4-Phenylazodiphenylamine (red-yellow)
4-Phenylazo-1-naphthylamine (red-yellow)
Phloxine B (red/brown-yellow)
Picric acid (yellow-colorless)
Poirrier Blue (blue-red)
Propyl Red (red-yellow)
1(2-Pyridylazo)-2-naphthol (red-yellow)
Pyrocatechol Violet (red-yellow)
Pyrogallol Red (deep yellow-colorless)
Pyrogallolpthhalein (pale-orange)
Pyrogallosulfonphthalein (yellow-colorless)
Quinoline Blue (colorless-blue)
Quinaldine Red (colorless-red)
Resazurin (red-blue)
Resorcin Blue (red-blue)

Resorcinol (red-blue)
4-(2-Pyridylazo)resorcinol monosodium salt (red-blue)
4-(2-Pyridylazo)resorcinol disodiun salt (red-blue)
Resorinol Yellow (Tropeolin 0) (yellow-orange/brown)
Rhodamine (orange/pink-violet)
Rosalic Acid (yellow/brown-red)
Rose Bengal (red-yellow)
Safanin (red-yellow)
SPADNS (varies)
Tartrazine (colorless-yellow)
Tartrazine Yellow (colorless-yellow)
Tashiro's indicator (red/brown-yellow)
Tetrabromophenol (yellow-brown)
Tetrabromophenolphthalein (yellow-brown)
Tetrabromophenolphthalein ethyl ester, potassium salt (yellow-brown)
3,4,5,6-Tetrabromophenolsulfonephthalein (yellow-brown)
3,3,5,5-Tetraiodophenolphthalein (yellow-brown)
3,3,5,5-Tetraiodophenolsulfonephthalein (yellow-brown)
Thiazole Yellow G (colorless-yellow)
Thorin (red/brown-yellow)
Thymol Blue (yellow-blue)
Thymol Blue Sodium Salt (red-yellow)
Thymolphthalein (colorless-blue)
Thymol Violet (yellow-green/violet)
Titan Yellow (yellow-red)
4-o-Tolyazo-o-toluidine (orange-yellow)
5,5'7-Trisulfonic acid tripotassium salt (yellow-colorless)
1,3,5-Trinitrobenzene (colorless-orange)
2,4,6-Trinitrobenzene (colorless-orange)
2,4,6 trinitrotoluene (colorless-orange)
Tropaeolin (yellow-orange/brown)
Universal indicator sticks (varies)
Xylene Orange Tetrasodium Salt (red-yellow)
Xylenol Blue (red-yellow)
Xylenol Orange (red-yellow)
Xylenecyanol FF (red-yellow)
MIXED INDICATORS:
  methyl yellow and methylene blue (in alc.) (blue/violet-green)
  xylene cyanol (in alc). and methyl orange (in aq.) (violet-green)
  methyl orange and indigo carmine (in aq.) (violet-green)
  methyl orange and aniline blue (in aq.) (violet-green)
  bromocresol green sodium and methyl orange (in aq.) (orange-blue/green)
  bromocresol green and methyl red (in aq.) (wine/red-green)
  methyl red and methylene blue (On alc.) red/violet-green)
  chlorophenol red sodium (in aq.) and aniline blue (in aq.) (green-violet)
  bromocresol green sodium and chlorophenol red sodium (in aq.) (green-violet)
  bromocresol purple sodium and bromothymol blue sodium (in aq.) (violet-blue)
  bromothymol blue sodium and azolitimin (in aq.) (violet-blue)
  neutral red and methylene blue (in alc.) (violet-blue/green)
  neutral red and bromothymol blue In alc.) (rose-green)
  cyanine and phenol red (in alc.) (yellow-violet)
  bromothymol blue sodium and phenol red sodium (in aq.) (yellow-violet)
  cresol red sodium and thymol blue sodium (in aq.) (yellow-violet)
  a-naphtholphthalein and cresol red (in alc.) (pale rose-violet)
  a-naphtholphthalein and phenolphthalein (in alc.) (pale rose-violet)
  phenolphthalein and methyl green (in alc.) (green-violet)
  thymol and phenolphthalein (in alc.) (yellow-violet)
  phenolphthalein and thymolphthalein (in alc.) (colorless-violet)
  phenophthalein and Nile blue (in alc.) (blue-red)
  thymolphthalein and alizarin yellow (in alc.) (yellow-violet)
  Nile blue (in aq.) and alizarin yellow (in alc.) (red-brown)
SCREENED INDICATORS:
  Dimethyl yellow and Methylene Blue (pink-yellow green)
  Methyl orange and Xylene-cyanol (mauve-green)
  Methyl orange and Aniline green (violet-green)
  Methyl orange and fluorescein (orange-green)
  Methyl red and Methylene blue (mauve-green)
  Chlorophenol red and Aniline Blue (green-violet)
  Neutral red and Methylene blue (blue violet-green)
  Phenolphthalein and Methyl green (green-violet)
  Phenol red and methylene blue (red-blue)
  Phenolphthalein and methyl green (colorless-green)
  Phenolphthalein and nile blue (colorless-blue)
  Nile blue and alizarin yellow (blue-yellow)
UNIVERSAL INDICATORS:
  There are many examples of universal indicators. They respond over a wide pH range. Examples are:
  Yamada's universal indicator (pH range 4–10, red-orange-yellow-green-blue-deep blue-violet)
  van Urk's universal indicator (pH range 2–8, orange/red-red-yellow-green/yellow-green)
NATURAL FOOD OR PLANT INDICATORS (derived from Red cabbage and purple cabbage):
  Red cabbage and purple cabbage (red yellow)
  Chinese Cabbage Kimchi (red-yellow)
  Radishes (red-yellow)
  Red Onions (red-yellow)
  Strawberrys (red yellow)
  Blackberries (red-yellow)
  Rasberries (red-yellow)
  Cranberries (red-yellow)
  Grapes (red-yellow)
  Plums (red-yellow)
  Cherries (red-yellow)
  Beets (red-yellow)
  Carnation flowers (varies)
  Purple Dahlias (purple-yellow)
  Purple Hollyhocks (purple -yellow)
  Red Geraniums (red-yellow)

Blue Iris (blue-yellow)
Hydrangeas (varies)
Roses (varies)
Pomergranates (red-yellow)
Native/non-poisonous plants (varies)

FLUORESCENT INDICATORS:
Benzoflavine (yellow-green)
3,6-Dioxyphthalimide (blue-green)
Eosine YS (yellow color-yellow flock)
Erythrosine (yellow color-yellow flock)
Esculin (colorless-blue)
4-Ethoxyacridone (green-blue)
3,6-Tetramethyldiaminooxanthone (green-blue)
Chromotropic acid (colorless-blue)
Fluorescein and derivatives like dichlorofluorescein (colorless-blue)
Magdala Red (purple color-purple flock)
a-Naphthylamine (colorless-blue)
b-Naphthylamine (colorless-violet)
Phloxine (colorless-bright yellow)
Salicylic acid (colorless-blue)
Acridine (green-violet)
Dichlorofluorescein (colorless-green)
3,6-Dioxyanthone (colorless-blue/violet)
Erythrosine (colorless-yellow/green)
b-Methylesculetin (colorless-blue)
Neville-Winther acid (colorless-blue)
Resorufin (yellow-weak orange)
Quininic acid (yellow-blue)
Quinine (yellow-violet)
Acid R Phosphine (yellow-red)
Brilliant Diazol Yellow (colorless-violet)
Cleves acid (colorless-green)
Coumaric acid (colorless-green)
3,6-Dioxyphthalic dinitrile (blue-green)
Magnesium 8-hydroxyquinolate (colorless-golden)
b-Methylumbelliferone (colorless-blue)
1-Naphth-4-sulfonic acid (colorless-blue)
Orcinaurine ((colorless-green)
Patent Phosphine (green-yellow)
Thioflavine (yellow color-yellow flock)
Umbelliferone (colorless-blue)
Acridine Orange (orange-green)
Ethoxyphenylnaphthostilbazonium chloride (green color-green flock)
G Salt (dull blue-bright blue)
Naphthazol derivatives (colorless-yellow/green)
a-Naphthionic acid (blue-green)
2-Naphthol-3,6-disulfonic acid (dark blue-light blue)
B-Naphthol (colorless-blue flock)
a-Naphtholsulfonic acid (dark blue-bright violet)
1,4-Naphthosulfonic acid (dark blue-light blue)
Orcinsulfonphthalein (yellow color-yellow flock)
Quinine (yellow-black)
R-Salt (violet-colorless)
Sodium 1-naphthol-2-sulfonate (dark blue-bright violet)
Coumarin (deep green-light green)
Eosine BN (colorless-yellow)
papaverine (permanganate oxidized) (yellow-blue)
Schaffers Salt (violet-green/blue)
SS-Acid (sodium salt) (violet-yellow)
Cotarnine (yellow color-white flock)
a-Naphthionic acid (blue-green)
b-Naphthionic acid (blue flock-green color)

LUMINESCENT INDICATORS:
Eosin (colorless-green)
Chromotropic acid (colorless-blue)
Fluorescein (colorless-green)
Dichiorofluorescein (colorless-green)
Acridine (green violet)
b-Naphthol (blue-violet)
Quinine (violet-colorless)

IRREVERSIBLE INDICATORS:
Amaranth (red-colorless)
Bordeaux (faint pink-yellow/green)
Brilliant Ponceaux (orange-colorless)
Napthol Blue Black (green-faint pink)

MISCELLANEOUS INDICATORS:
Chemiluminescent indicators such as luminol, lucigenin and lophine (varies)
SNARF pH indicators (varies)
NERF pH indicators (varies)
Dextran indicators (ex. fluoescein tetramethylthrodamine dextran) (varies)
Lipophilic indicators (varies)
Reactive indicators (varies)
Lysosensor indicators (varies)
Rhodol derivatives (varies)
Radical Scavenger indicators (varies)
Coffee extracts (varies)
Tea extracts (varies)
Herb extracts (varies)

The color combinations after each indicator show the color change the indicator undergoes with a change in pH from exposure to $CO_2$ produced by bacterial growth. The first color is the base color and the second, the exposed or changed color.

Some of the mixed indicators provide very distinct color changes associated with pH changes. These would be advantageous for use at the consumer level.

Natural indicators can be derived from a variety of foods and plants. The class of compounds called anthocyanines change color over different pH ranges and would therefore change color as a result of $CO_2$ production by bacteria. The above list includes examples of foods from which a pH indicator can be prepared. Also included are flower pedals, fruits, and fruit juices. The great advantage of natural indicators is that they are less likely to be associated with risks for most consumers.

Fluorescent indicators can display greater sensitivity and these may be extremely useful at the production level. This category of indicators show definite changes in fluorescense with change in pH as caused by $CO_2$ production by bacteria. Luminescent and chemiluminescent indicators show detectable changes in pH measurable by ultraviolet light and may also be especially useful at the production level.

The utilization of irreversible indicators in our innovation may offer the safest and most definitive method to detect the presence of bacteria in food. This could be relevant if the packaging is $CO_2$ permeable and $CO_2$ migrates outward. An irreversible indicator, once its color is changed by a change in pH, will not revert to its original color.

Radical scavenger indicators are detectable by UV or visible absorption or fluorescense equipment and may be more suitable for the detection of bacteria at the production level.

The invention disclosed herein is not only applicable to the detection of bacteria to prevent foodborne illness from consumable solids and liquids, but may also be used for other related purposes such as insuring sterile medical packaging, the safety of surgical suites, biological weapons detection and drug testing. The invention is accordingly defined by the following claims.

What is claimed is:

1. A device for detecting bacterial growth in a selected substance wherein a byproduct of said growth is carbon dioxide and wherein said carbon dioxide in the presence of ambient water results in the production of carbonic acid yielding an increase in hydrogen ion concentration and a decrease in pH, said device comprising in combination:

a. a $CO_2$ impermeable transparent support base;
    b. a quantity of an indicator having the property of exhibiting a color change upon exposure to a decrease in pH disposed upon said base;
    c. a $CO_2$ permeable cover disposed over said indicator and said base; said base, indicator and cover forming a composite which when said cover is placed in proximity to said substance will provide an indication of bacterial growth though an observable color change of said indicator.

2. The device of claim 1 wherein said indicator is combined with a gel.

3. The device of claim 2 wherein said indicator comprises an acid base indicator.

4. The device of claim 2 wherein said indicator comprises a mixed indicator.

5. The device of claim 2 wherein said indicator comprises a screened indicator.

6. The device of claim 2 wherein said indicator comprises a universal indicator.

7. The device of claim 2 wherein said indicator comprises a plant derived indicator.

8. The device of claim 2 wherein said indicator comprises a fluorescent indicator.

9. The device of claim 2 wherein said indicator comprises a luminescent indicator.

10. The device of claim 2 wherein said indicator comprises an irreversible indicator.

11. The device of claim 2 wherein said indicator comprises a miscellaneous indicator.

12. The device of claim 1 wherein said composite comprises a sheet food wrap.

13. The device of claim 1 wherein said composite comprises a portion of a container for liquids.

14. The device of claim 1 wherein said composite comprises a wafer for placement in the contact with said substance.

15. A method for detecting bacterial growth in a selected substance wherein a byproduct of said growth is carbon dioxide and wherein said carbon dioxide in the presence of ambient water results in the production of carbonic acid yielding an increases in hydrogen ion concentration and a decrease in pH, said method comprising in combination:

a. providing a $CO_2$ impermeable transparent support base;
    b. providing a quantity of an indicator having the property of exhibiting a color change upon exposure to a disease in pH and disposing said indicator upon said base;
    c. providing a $CO_2$ permeable cover and disposing said cover over said indicator and said base to provide a composite; and
    d. placing said composite and said cover in proximity to said substance to provide an indication of bacterial growth though an observable color change of said indicator.

16. The method of claim 15 wherein said indicator is combined with a gel.

17. The method of claim 16 wherein said indicator comprises an acid base indicator.

18. The method of claim 16 wherein said indicator comprises a mixed indicator.

19. The method of claim 16 wherein said indicator comprises a screened indicator.

20. The method of claim 16 wherein said indicator comprises a universal indicator.

21. The method of claim 16 wherein said indicator comprises a plant derived indicator.

22. The method of claim 16 wherein said indicator comprises a fluorescent indicator.

23. The method of claim 16 wherein said indicator comprises a luminescent indicator.

24. The method of claim 16 wherein said indicator comprises an irreversible indicator.

25. The method of claim 16 wherein said indicator comprises a miscellaneous indicator.

26. The method of claim 15 wherein said composite comprises a sheet food wrap.

27. The method of claim 15 wherein said composite comprises a portion of a container for liquids.

28. The method of claim 15 wherein said composite comprises a wafer for placement in contact with said substance.

* * * * *